(12) United States Patent
Elenbaas et al.

(10) Patent No.: US 11,896,411 B2
(45) Date of Patent: Feb. 13, 2024

(54) ADAPTIVE ANTI-SCATTER DEVICE

(71) Applicant: KONINKLIJKE PHILIPS N.V., Eindhoven (NL)

(72) Inventors: Thijs Elenbaas, Nijmegen (NL); Markus Johannes Harmen Den Hartog, Eindhoven (NL); Javier Olivan Bescos, Eindhoven (NL); Gereon Vogtmeier, Aachen (DE); William Edward Peter Van Der Sterren, Eindhoven (NL); Daniël Simon Anna Ruijters, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 369 days.

(21) Appl. No.: 17/282,052

(22) PCT Filed: Sep. 26, 2019

(86) PCT No.: PCT/EP2019/075974
§ 371 (c)(1),
(2) Date: Apr. 1, 2021

(87) PCT Pub. No.: WO2020/069950
PCT Pub. Date: Apr. 9, 2020

(65) Prior Publication Data
US 2021/0338183 A1 Nov. 4, 2021

(30) Foreign Application Priority Data
Oct. 4, 2018 (EP) .................................... 18198702

(51) Int. Cl.
*A61B 6/00* (2006.01)
*B33Y 80/00* (2015.01)
(Continued)

(52) U.S. Cl.
CPC .......... *A61B 6/4291* (2013.01); *A61B 6/4452* (2013.01); *A61B 6/54* (2013.01);
(Continued)

(58) Field of Classification Search
CPC ....... A61B 6/4291; A61B 6/4452; A61B 6/54; A61B 6/4441; B33Y 80/00; G21K 1/025; G21K 1/04
See application file for complete search history.

(56) References Cited

U.S. PATENT DOCUMENTS 5,291,539 A    3/1994 Thumann
6,470,072 B1  10/2002 Johnson
(Continued)

FOREIGN PATENT DOCUMENTS

EP    0040158 A1   11/1981
JP    2000217813 A  8/2000
WO    2018037128 A1  3/2018

OTHER PUBLICATIONS

International Search Report and Written Opinion of PCT/EP2019/075974, dated Nov. 27, 2019.

*Primary Examiner* — Kiho Kim

(57) ABSTRACT

An adaptive X-ray anti-scatter device for placement in a source-detector axis of an X-ray imager includes an anti-scatter filter having a source orientable surface and a detector orientable surface. The anti-scatter filter comprises a plurality of realignable slats that absorb incident X-rays and are separated by a plurality of interstitial portions. The device also includes a first actively deformable member comprising a first set of one or more actively deformable actuators disposed across a first region of the first actively deformable member. At least a portion of the first set is partially or fully recessed within the interstitial portions. At least one actuator of the first set is in contact with a corresponding realignable slat of the plurality of realignable (Continued)

slats and is configured to change the alignment of the corresponding realignable slat in relation to the source-detector axis.

14 Claims, 8 Drawing Sheets

(51) Int. Cl.
  *G21K 1/02* (2006.01)
  *G21K 1/04* (2006.01)
(52) U.S. Cl.
  CPC .............. *B33Y 80/00* (2014.12); *G21K 1/025* (2013.01); *G21K 1/04* (2013.01); *A61B 6/4441* (2013.01)

(56) References Cited

U.S. PATENT DOCUMENTS

| | | | |
|---|---|---|---|
| 7,127,038 B2 | 10/2006 | Kondradsson | |
| 2007/0064878 A1* | 3/2007 | Heismann | G21K 1/025 378/154 |
| 2009/0272874 A1 | 11/2009 | Appleby | |
| 2019/0343471 A1* | 11/2019 | Kok | G02B 1/04 |

* cited by examiner

# ADAPTIVE ANTI-SCATTER DEVICE

CROSS-REFERENCE TO PRIOR APPLICATIONS

This application is the U.S. National Phase application under 35 U.S.C. § 371 of International Application No. PCT/EP2019/075974, filed on Sep. 26, 2019, which claims the benefit of European Patent Application No. 18198702.5, filed on Oct. 4, 2018. These applications are hereby incorporated by reference herein.

FIELD OF THE INVENTION

This application relates to an adaptive X-ray anti-scatter device for placement in the source-detector axis of an X-ray imager, an X-ray detector, an X-ray imaging system, a method for manufacturing an adaptive anti-scatter device, a computer program element comprising instructions for the operation of a 3D or 4D printer, and a computer readable medium comprising instructions for the operation of a 3D or 4D printer.

BACKGROUND OF THE INVENTION

To resolve structures in an X-Ray image of a region of interest of a patient, it is important that the X-Ray radiation incident on a given portion of an X-Ray detector has travelled in a straight line between an X-Ray source and the given portion of the X-Ray detector. However, the passage of X-rays through different types of tissue in a patient causes scattering of the X-Ray beam. This scattering can degrade the quality of a received X-Ray image. Accordingly, anti-scatter grids are provided in X-Ray imaging systems to reduce or to eliminate scattered X-Ray radiation.

WO 2018/037128 A1 discusses a variable focus X-Ray anti-scatter device, although such equipment may be further developed.

SUMMARY OF THE INVENTION

The object of the present invention is solved by the subject-matter of the independent claims. Further exemplary embodiments are evident from the dependent claims in the following description.

Therefore, according to a first aspect of the invention, there is provided an adaptive anti-scatter device for placement in the source-detector axis of an X-ray imager. The adaptive anti-scatter device comprises:

an anti-scatter filter having a source orientable surface and a detector orientable surface. The anti-scatter filter comprises a plurality of realignable slats for absorbing incident X-rays. The slats are separated by a plurality of interstitial portions. The adaptive anti-scatter device also comprises:

a first actively deformable member comprising a first set of one or more actively deformable actuators disposed across a first region of the first actively deformable member.

At least a portion of the first set of one or more actively deformable actuators of the first set of actively deformable actuators is partially or fully recessed within the interstitial portions of the anti-scatter filter. Further, at least one actuator of the first set is configured to change the alignment of a corresponding slat of the anti-scatter filter in relation to the source-detector axis. More in particular, the actuator may be in contact with at least one realignable slat of the plurality of slats, so that a deformation of the actuator causes the corresponding change to the alignment of the corresponding slat, for example from a first alignment to a second alignment relative to the source-detector axis.

Accordingly, it is possible to vary an angulation of slats in an adaptive anti-scatter device as a function of the source-image distance. This ensures that for each setting of the source-image distance in an X-Ray imager, scattered X-Rays are blocked from impinging on inappropriate sections of an X-Ray detector. Therefore, the adaptive anti-scatter filter enables the provision of high-quality X-Ray images from a wide range of source image distances. Furthermore, the structure of the adaptive anti-scatter device according to the first aspect is suitable for manufacturing using a 3D or 4D printing process, enabling cost and efficiency savings when manufacturing the adaptive anti-scatter device. Because at least a portion of each actuator of one or more of the first set of one or more actively deformable actuators is partially or fully recessed within the interstitial portions, the X-Ray anti-scatter filter is compact, and simpler to manufacture.

Optionally, the adaptive anti-scatter device further comprises a cover element that is translucent to X-rays arranged to cover at least one side of the adaptive anti-scatter device. The slats of the anti-scatter filter are coupled to the cover element.

Accordingly, the realignable (tiltable) slats of the anti-scatter filter may be protected from one, or both sides from mechanical damage or the ingress of dust or foreign objects, for example.

Optionally, the lateral spatial density of actively deformable actuators of the first actively deformable member varies as a function of the lateral location on the first actively deformable member.

Accordingly, a greater proportion of X-rays directly in line with the X-Ray source can be directed to a geometrically appropriate portion of an X-Ray detector, and a greater proportion of scattered X-rays are be rejected.

Optionally, the first actively deformable member further comprises a second set of one or more actively deformable actuators disposed in a second region of the first actively deformable member. The first region is laterally closer to the source-detector axis than the second region. The second region of the first actively deformable member comprises a greater spatial density of actively deformable actuators than the first region.

Accordingly, because the second region of the first actively deformable member has a greater spatial density of actively deformable actuators, the second region will deform to a greater extent than the first region upon the application of a driving signal. Because the second region is located laterally further away from the source-detector axis compared to the first region, the realignable (tiltable) slats (lamellae) may be altered appropriately to reject scattered X-rays effectively for every lateral location of the X-Ray detector.

Optionally, the anti-scatter device further comprises a second actively deformable member comprising a third set of one or more actively deformable actuators configured to change the alignment of a corresponding slat of the anti-scatter filter in relation to the source-detector axis. Each actively deformable actuator of the third set of one or more actively deformable actuators is formed within the interstitial portions of the anti-scatter filter and in contact with at least one corresponding slat of the plurality of slats, so that a deformation of one or more of the third set of one or more actively deformable actuators causes a corresponding change to the alignment of the at least one corresponding slat relative to the source-detector axis.

Accordingly, a further layer of deformable actuators may be provided having a different deformation ratio compared to the initial layer of deformable actuators.

Optionally, the second actively deformable member is located closer to the source-orientable face than the first actively deformable member. The lateral spatial density of actively deformable actuators of the second actively deformable member is greater than the lateral spatial density of the actively deformable actuators of the first actively deformable member at corresponding lateral positions of the first and second deformable members.

Accordingly, the portions of slats (lamellae) that are closer to the source may be moved (tilted) a greater distance compared to portions of slats that are further from the source.

Optionally, the interstitial spaces of the anti-scatter filter comprise actuators of the first and/or second actively deformable member, wherein each interstitial space comprises a first set of one or more actively deformable actuators, and a second plurality of non-deformable actuators, or actuators that are less deformable than the actuators in the first set of one or more actively deformable actuators.

Accordingly, the expansion ratio inside the interstitial spaces can be carefully controlled by providing a greater or smaller proportion of actively deformable actuators compared to non-deformable (or less-deformable) actuators.

Optionally, the actuators of the first and/or second actively deformable member are controllable with a unified control signal, or the actuators of the first and/or second actively deformable member are divided into individually addressable actuator regions.

Accordingly, the actuators of the first and/or second actively deformable member may be driven by a control signal that is at least partially a function of the source-detector distance of an X-Ray imaging system using the adaptive anti-scatter filter. In the case of a control signal enabling the individual addressing of actuator regions, a fine control of the slat (lamellae) tilt ratio is possible. In the case that a unified control signal is used to actuate every actuator region simultaneously, a low-cost (simpler) signal control approach is possible.

Optionally, at least one of the first, second, and/or third pluralities of actively deformable actuators comprise actively deformable actuators of an electro-active or thermally-active polymer or metal alloy.

Accordingly, the actuators may be produced using materials that are compatible with 3D or 4D printing techniques.

Optionally, the actively deformable actuators are configured to shrink in the plane parallel to the lateral face of the adaptive anti-scatter device under the influence of an actuating signal.

Optionally, the actively deformable actuators are configured to expand in the plane parallel to the lateral face of the adaptive anti-scatter device under the influence of an actuating signal.

Optionally, the set of one or more actively deformable actuators of the first actively deformable member comprises one or more actively deformable actuators configured to shrink in the plane parallel to the lateral face of the adaptive anti-scatter device, and a one or more actively deformable actuators configured to expand in the plane parallel to the lateral face of the adaptive anti-scatter device, under the influence of an actuating signal.

Accordingly, fine control of the placement of respective actuator groups that can expand or contract enables the fine-tuning of the deflection pattern of the adaptive anti-scatter filter and the provision of more complicated deflection patterns.

According to a second aspect, there is provided an X-ray detector assembly comprising:
   an X-ray detector, and
   at least one anti-scatter device according to the first aspect or its embodiments.

Accordingly, such an X-Ray detector assembly can adaptively change its scatter rejection characteristic based at least partially on the source to distance ratio of a system that the X-Ray detector assembly is used inside.

According to a third aspect, there is provided an X-ray imaging system having a variable source-imaging distance comprising:
   an X-ray source configured to emit a beam of X-ray radiation directed towards a patient imaging area of the X-ray imaging system along a source-detector axis;
   an X-ray detector assembly according to the second aspect configured to detect X-ray radiation emitted from the X-ray source; and
   a controller configured to provide a control signal to the first actively deformable member of the anti-scatter device of the X-ray detector.

The X-ray source and/or the X-ray detector are configurable so that they can be separated by at least a first and a second different source detector distance.

The controller is configured to monitor the source detector distance of the X-ray source and X-ray detector, and to generate a control signal for the first actively deformable member, to set the first actively deformable member using the control signal, and to obtain X-ray imaging data from the X-ray detector with the first actively deformable member configured at an appropriate alignment for the source detector distance of the X-ray source and X-ray detector.

Accordingly, an X-Ray imaging system according to the third aspect is capable of providing images with significant scatter reduction even though the source to detector distance is variable.

According to a fourth aspect, there is provided a method for manufacturing an adaptive anti-scatter device comprising:
   a) providing an anti-scatter filter having a source orientable surface and a detector orientable surface, wherein the anti-scatter filter comprises a plurality of realignable slats for absorbing incident X-rays, wherein the realignable slats are separated by a plurality of interstitial portions; and
   b) providing a first actively deformable member comprising a first set of one or more actively deformable actuators disposed across a first region of the first actively deformable member. This step further includes:
   providing at least a portion of the first set of one or more actively deformable actuators within the interstitial portions of the anti-scatter filter in a partially or fully recessed manner, and contacting at least one actuator of the first set of one or more actively deformable actuators with at least one realignable slat of the plurality of slats such that a deformation of the at least one actuator causes a change of the alignment of the corresponding slat in relation to the source-detector axis.

Accordingly, an adaptive anti-scatter device having integral actuation can be manufactured, leading to a more compact and easy to produce adaptive anti-scatter device.

Optionally, either or both of a) and/or b) are performed using a 3D or a 4D printer. In other words, either or both providing steps may comprise additive manufacturing by means of a 3D or 4D printer.

Accordingly, the adaptive anti-scatter device may be produced substantially automatically, for example being controlled through a set of suitable instructions for operation of such printer.

Optionally, the anti-scatter filter is an anti-scatter grid.

According to a fifth aspect, there is provided a computer program element comprising instructions for the operation of a 3D or 4D printer which, when addressed to a 3D or 4D printer, cause the 3D or 4D printer to follow the method of the fourth aspect.

According to a sixth aspect, there is provided a computer readable medium comprising instructions for the operation of a 3D or 4D printer of the fifth aspect.

In this application, the term "adaptive anti-scatter device" means an anti-scatter filter for use in an X-Ray imaging system having realignable slats (lamellae). Realignment of the slats enables adaptive spatial filtering of X-Ray scatter, which varies as the source to detector distance is adjusted. Most preferably this adaptation occurs as at least a partial function of the source to detector separation distance of an X-Ray imaging system. The most common form of an anti-scatter device is a rectangular or square grid of X-Ray opaque material comprising slats that are angled with respect to the source to detector direction. However, filtering performance may also arise using an anti-scatter device having a single dimension of angled slats (in the manner of a comb) which can benefit from the technique discussed herein, and thus the provision of an anti-scatter filter in a grid form is not essential.

In this application, the term "realignable slat" refers to a tiltable lamella, that when built up into a filter can filter scattered X-rays. Accordingly, the realignable slats may be provided as lamellae of lead or molybdenum, for example. The fact that the slats are "realignable" means that there are each configurable into a range of angles with respect to a lateral (x-y) plane of the adaptive anti-scatter device. This realignment may, for example, be enabled by gluing a strip of resilient polymer to a lead or molybdenum wafer strip, to enable the slat (lamella) to reorient with respect to the source detector axis.

Optionally, the slats are realignable between being perpendicular to the lateral plane to being aligned so as to form an enclosed angle between the realignable slat and the lateral plane of the anti-scatter device in the ranges: 90 degrees to 85 degrees, 90 degrees to 80 degrees, 90 degrees to 75 degrees, 90 degrees to 70 degrees, 90 degrees to 65 degrees, 90 degrees to 60 degrees. It is not required that all slats are simultaneously at the same alignment. For example, at a specific source to detector distance, the relative angulation of each slat to its predecessor may increment by a certain amount as a given position on the lateral plane of the adaptive anti-scatter filter moves away from a source to detector axis to account for X-ray optics.

In this application, the term "interstitial portion" refers to the region in between neighboring realignment slats (lamellae). Optionally, the interstitial portion is empty (comprises air), or interstitial portion may comprise a compressible filler material such as paper, foam, rubber, or the like. The filling of the interstitial portions may vary over different lateral portions of the adaptive anti-scatter device.

In this application, the term "actively deformable member" comprises a portion of material that upon the application of a driving signal can change its shape by expanding, or contracting, and transmit a force to an abutting item whilst doing so. The "actively deformable member" is disposed at least partially in the interstitial portions of the anti-scatter filter, although in some embodiments an actively deformable member may be entirely comprised inside the interstitial portions. The actively deformable member is capable of changing the orientation of a plurality of slats of an anti-scatter filter, and thus typically is a sheet-like member capable of insertion or partial insertion into the interstitial portions of an anti-scatter filter. In one option, the actively deformable member comprises a layer of actively deformable material having one side with upstanding linear vanes corresponding to interstitial portions of an anti-scatter grid. The vanes are pushed into their respective interstitial spaces so as to abut the realignable slats. The actively deformable member may also be an internal layer that is 3D printed into the interstitial portions.

At least a portion of the actively deformable member is in contact with the anti-scatter filter, such that when the actively deformable member expands or contracts, a realignment in the anti-scatter filter is affected.

Optionally, the actively deformable member may be comprised of an actuator material that expands or contracts in the presence of thermal energy. Optionally, the actively deformable member may be comprised of an actuator material that expands or contracts under the application of an electrical field, a potential difference, or a magnetic field. Optionally, the actively deformable member may be a microfluidic element such as a microfluidic bladder, optionally fabricated from rubber or silicone, that expands and contracts as gas or fluid is pumped into or out of the bladders, respectively. Optionally, the actively deformable member may be an auxetic structure wherein a small mechanical actuation causes a much larger affirmation response. Optionally, the actively deformable member may be comprised of any combination of the above techniques. Optionally, the actively deformable member is an electroactive polymer, preferably comprising a monomer selected from the group consisting of vinylidene fluoride and trifluorovinyl. Optionally, the actively deformable member is a shape-memory alloy such as copper-aluminium-nickel, or nickel-titanium alloy. Thus, the actively deformable member can be configured to move from an initial expanded position to a contracted position, or to begin from an initial contracted position and expand (deformation is considered in the following application has meaning shrinking or expanding, as the context requires).

In the following application, the term "actively deformable actuator" defines the simplest unit of space of an "actively deformable member" capable of affecting a change of shape of the actively deformable member. In other words, several actively deformable actuators may be assembled into the interstitial space, with at least one actively deformable actuator in contact with a realignable slat (lamella). Of course, the deformable actuators will themselves change in volume as they undergo deformation. Optionally, the actuators are substantially cubic, although the application is not so limited and substantially any shape producible using, for example, a 3D or 4D printer may be applied. Alternatively, the term "actively deformable actuator" may be interpreted as an "actively deformable voxel", meaning a portion of 3D space that can change shape, and exert a force against a realignment or slat upon the application of the driving signal. Optionally, the actively deformable actuator may comprise an auxetic cell.

The activation of a thermal actuator material can be performed using different temperature levels. A temperature difference may be used to switch the actuator between a first and a second position (or even a range of positions in-between). In this option, a thermal actuator material used in the actuator of an adaptive anti-scatter grid could be generated by local heating elements which could be part of the carrier element as homogenous heating foils, heating wires, and/or local heating elements which could be printed by conductive material and connected to a central programmable power supply (or via matrix controller having individually addressable sub-segments).

Optionally, the actuator material could comprise pre-deformed metal foils in the manner of the spring, alternatively the use of bi-metal springs.

In the following application, the term "lateral spatial density" refers, for example, to the ratio between an area of an actively deformable member of actuators versus a passive area over a given layer of the adaptive anti-scatter filter. For example, a layer comprising an actively deformable layer axially closer to the X-ray detector in use may optionally have a higher lateral spatial density of actively deformable actuators compared to an actively deformable layer axially further away from to the X-ray detector in use, enabling the ends of the slats closer to the X-Ray detector to have their divergence adjusted to a greater degree compared to the ends of the slats closer to the X-Ray source.

In the following application, the term "partially or fully recessed" refers to the alignment of an actively deformable member relative to the slats of the anti-scatter device. A given portion of the actively deformable member must be able to transfer a substantially transverse force (relative to the source to detector axis) to the realignable slats of anti-scatter device. Typically at least one actively deformable actuator of the actively deformable member abuts a realignable slat, enabling direct transfer of the transverse force to the realignable slat. However it is also foreseeable that a portion of inert material could transfer the transverse force to the realignable slat from an actively deformable actuator. Because a portion of the actively deformable member abuts one or more realignable slats, the actively deformable actuator should, in one option, be placed as a layer entirely within the interstitial portions of the anti-scatter filter. Optionally, an actively deformable member can be located across the source orientable surface and/or across the detector orientable surface, with extensions abutting the one or more realignable slats at least partially extending into the interstitial portions. For example, the extensions may extend into the interstitial portion by 5%, 10%, 15%, or 20% or the total depth of the slat height (substantially in the direction of the source-detector axis).

In the following application, the term "3D printer" refers to a machine for additively manufacturing parts using the sequential deposition of layers of material according to a computer program, or list of computer instructions. Different types of materials (such as plastics and metals) may be deposited in intricate and complicated patterns, allowing the manufacture of an adaptive anti-scatter filter as described herein.

In the following application, the term "4D printer" refers to a machine for additively manufacturing parts using the sequential deposition of layers of material according to a computer program, or list of computer instructions. Different types of materials (such as plastics and metals) may be deposited in intricate and complicated patterns, allowing the manufacture of an adaptive anti-scatter filter as described herein. However, such a printer is capable of generating complicated shapes that are able to change their physical form in response to one or more of a thermal, mechanical, electrical stimulus for example. An auxetic element is one example of the output of such a 4D printer.

Accordingly, a basic idea to be discussed further in the application is that an adaptive anti-scatter filter (grid) having, for example, a mixture of inactive and active voxels (actuators) that cause the grid members to change their angulation upon the application of an external signal at least partially related to the source detector separation of an X-Ray imaging system. This enables the focal distance of the anti-scatter grid to be made equal to the source to image distance at every source to image distance setting, enabling the image quality obtained from an X-Ray detector using the adaptive anti-scatter grid to be improved because less primary radiation is absorbed due to defocus.

DETAILED DESCRIPTION OF EMBODIMENTS

Figure 1:
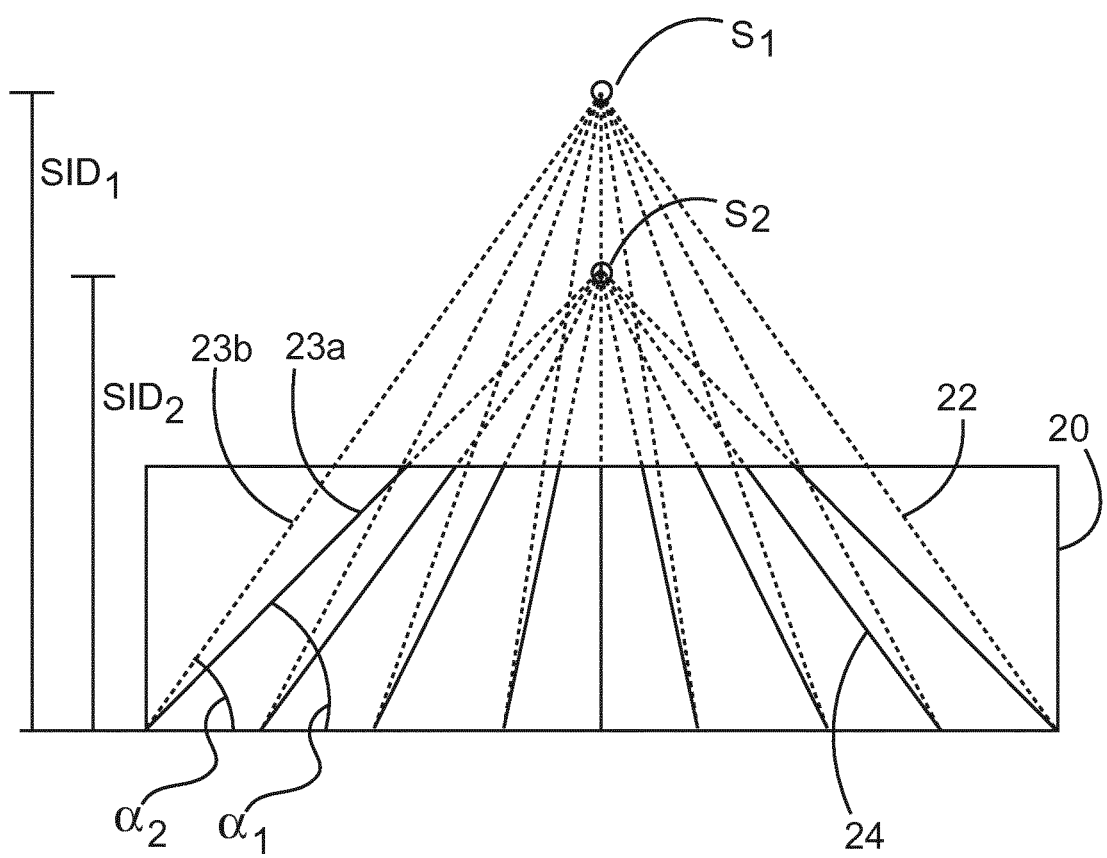
FIG. 1 schematically illustrates a side-view of a conventional anti-scatter grid.

Many X-Ray systems have a variable source to image distance (SID). Examples of such systems are, for example, A C-arm system (as depicted in FIG. 1), or other types of digital X-Ray imagers (such as mammography scanners) with adjustable distances between the source and detector. Such systems typically comprise an anti-scatter grid having slats (lamellae) at a fixed orientation. This orientation is chosen, for example, to exclude an optimum amount of scatter at a specific source to image distance of the X-Ray imager (for example, the statistically most commonly used soft image distance).

FIG. 1 illustrates an exaggerated example of how grid slats (lamellae) should be ideally focused as the SIG changes. In FIG. 1, a schematic side view of a fixed anti-scatter grid 20 is shown. The array of lines 23b illustrate the optimal alignment of the slats (lamellae) for source image distance $SID_1$. The array of lines 23a illustrate the optimal alignment of the slats (lamellae) for source image distance $SID_2$. As the source to image distance becomes closer to the anti-scatter grid 20, the enclosed (acute) angle $\alpha_1$ between the extreme left slat in its first position 23a and the base of the anti-scatter grid is smaller as compared to the enclosed (acute) angle $\alpha_2$ between the extreme slat in its second position 23b and the base of the anti-scatter grid. Thus, a typical anti-scatter grid having fixed slats can only be optimized to have optimum anti-scatter performance at a single source detector separation.

This application proposes that the slats (lamellae) of the grid are oriented such that they are parallel, or substantially parallel, to the incoming beams from the source of many different source to image distances across the lateral face of an X-Ray detector.

In systems with a variable source to image distance, the grid function of a normal non-flexible anti-scatter grid is severely hampered at source to image distance settings which differ from the nominal grid focus. As a compromise, the grid parameters, most notably the grid ratio, must be chosen to be relatively low. This enables the anti-scatter grid to function at the boundary of the allowed source to image distance range this reduces the overall performance of the grid, and makes it less selective for discriminating primary (useful) from secondary (scatter) radiation as compared to a single fixed SID system.

Figure 2:
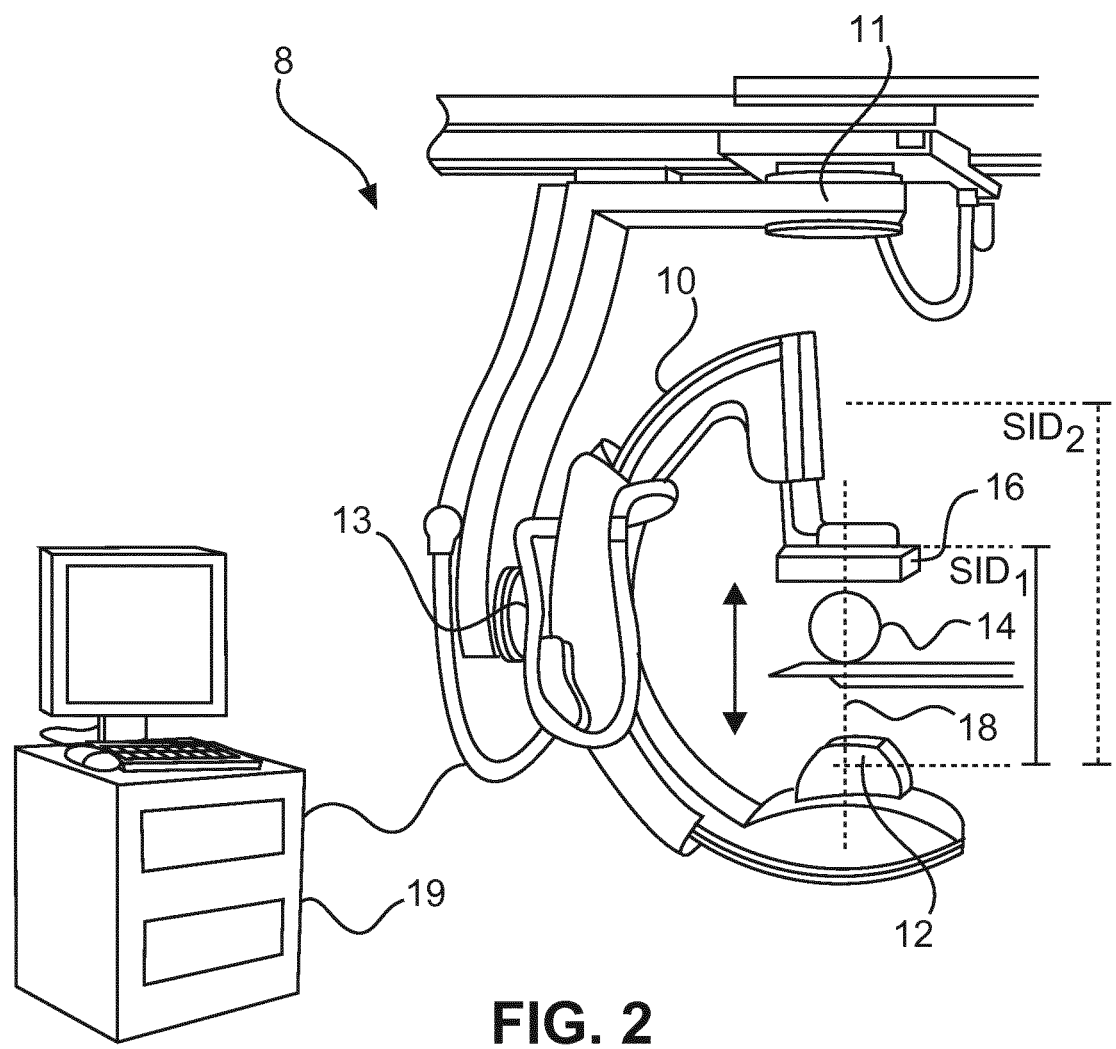
FIG. 2 schematically illustrates a C-arm X-Ray imaging system according to an example of the third aspect.

FIG. 2 illustrates an example of an X-Ray imaging system according to a third aspect. In this case, the system is C-arm although this application is addressed to any X-Ray imaging system with a variable source to imager distance. The X-Ray imaging system comprises a C-arm 10 supporting an X-Ray source 12 configured to emit X-rays in a beam through a region of interest 14 that may contain a patient in use. The C-arm 10 further comprises an X-Ray detector 16 comprising an adaptive anti-scatter grid (not shown in FIG. 2) according to a first aspect. The C-arm 10 is physically supported from the ceiling via an azimuth joint 11 and a tilt joint 13, enabling the positioning of the C-arm into a variety of positions around the region of interest 14. Furthermore, one or both of the X-Ray source 12 and the X-Ray detector 16 may be repositionable between at least a first source to image distance $SID_1$ and a second source to image distance $SID_2$. Preferably, the repositioning of the X-Ray source 12 relative to the X-Ray detector is along a source to detector axis 18 that is orthogonal both to a plane containing the X-Ray detector 16 and the X-Ray source 12 however, it will be appreciated that the adaptive anti-scatter grid may also be applied in arrangements where the X-Ray detector 16 and/or X-Ray source 12 are slightly misaligned. The X-Ray imaging system also comprises a controller 19 connected to the C-arm 10. The controller 19 is capable of accurately controlling the orientation of the C-arm 10 and the source to image distance of the X-Ray source 12 and the X-Ray detector 16. Furthermore, the controller may generate control signals for the adaptive anti-scatter device based on the source to image distance of the X-Ray source and X-Ray detector 16.

Accordingly, if the slats (lamellae) of an anti-scatter device are not perfectly oriented towards the plane of the X-Ray source 12, a part of the direct radiation will intersect with the slats and be absorbed. The amount of absorption depends on the slat depth and the misalignment angle.

Accordingly, a solution to this problem is to provide a variable focus grid in which the focal distance of the grid can be matched to the actual source to image distance across a range of source to image distances. For such grids, a higher aspect ratio can be chosen which reduces the amount of scatter in the X-Ray image and improves image quality for each source to image distance.

An insight of this application is that every slat (lamella) requires a specific and different angulation based on its lateral separation distance from the source to image axis (focal spot) of the X-Ray imaging system 10. Furthermore, the rate of change of each interior angle of each slat (lamella) with respect to the source to image distance will be different. Accordingly, fine-grained control of the angulation of each slat (lamella) is required as the source to image distance changes. In other words, it is proposed to provide individually tuned lamella steering. In principle, it is proposed to use 3D or 4D printing to partially or fully fill the interstitial spaces between slats (lamella) using smart materials, or a combination of smart materials and inert materials.

Smart materials respond to external stimuli by transforming their shape and/or volume and changing their physical properties (for example, Young's modulus, stiffness, and resistance) in particular, smart materials that exhibit the shape-memory effect are able to recover their original shape following environmental transformation.

The recently developed techniques of 3D or 4D printing allow an accurate positioning of smart materials at least partially within the interstitial spaces of an anti-scatter grid to enable fine movements and deformations to be made. For example, a printer such as the Stratasys Polyjet™ enables small actuators to be provided inside, or partially inside, the interstitial spaces of an anti-scatter grid (voxel print technology). Using more advanced 3D or 4D printers, it is possible to print or deposit the slats (lamellae) of the anti-scatter grid and the interstitial actuators in a single 3D or 4D printer, for example.

Figure 3A:
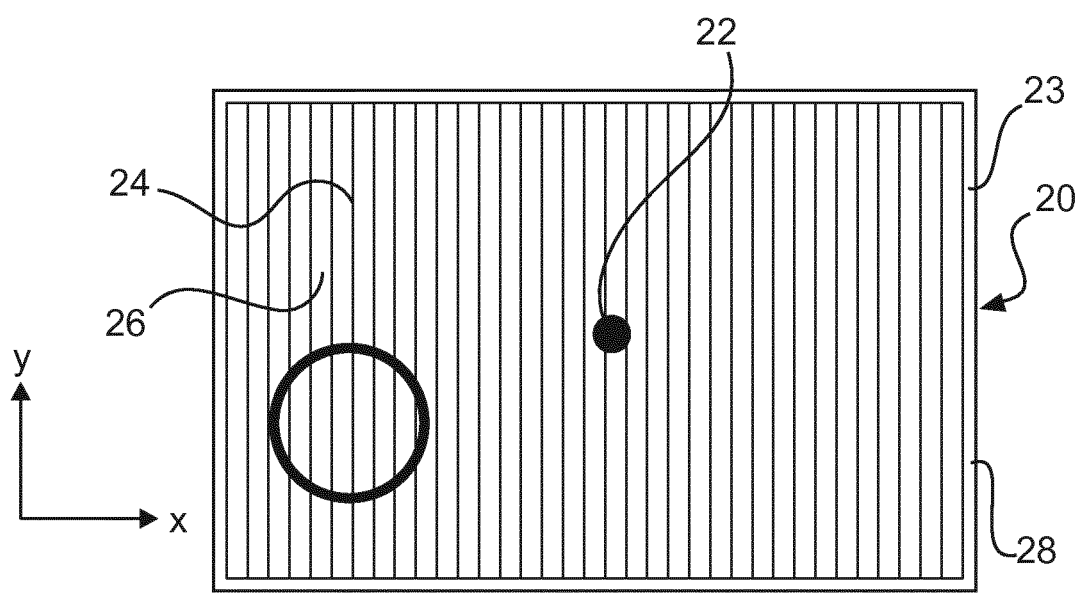
FIG. 3a) schematically illustrates a front view of an exemplary anti-scatter grid according to the first aspect.

FIG. 3a) schematically illustrates the front face of an adaptive anti-scatter device 20 according to a first aspect. In other words, an X-Ray source would be directed above the page looking down towards the anti-scatter grid. The adaptive anti-scatter device 20 may be placed in the source-detector axis of an X-Ray imager. An example position 24 of the source-detector axis at a central portion of the adaptive anti-scatter device 20 is illustrated, although it will be appreciated that the source-detector axis 22 can be offset from this position. Thus what is illustrated is a source orientable surface. The reverse (not visible) is a detector orientable surface. The majority of the area of the adaptive anti-scatter device comprises a plurality of realignment slats 24 in the y direction. Although illustrated as a rectangular grid with regular spacing, the realignable slats (lamellae) may optionally be spaced irregularly, and oriented diagonally, for example.

The realignable slats 24 are fabricated from a material that functions to interrupt scattered X-Ray radiation. In particular, the slats may be formed from lead, tungsten, bismuth, molybdenum, or alloys thereof. Thus, the gaps in between the slats comprise interstitial spaces 26. The surround of the adaptive anti-scatter device may optionally comprise a support frame 28, although in some implementations the anti-scatter grid may be supported directly in the chassis of an X-Ray detector and does not require an integral support frame 28.

Figure 3B:
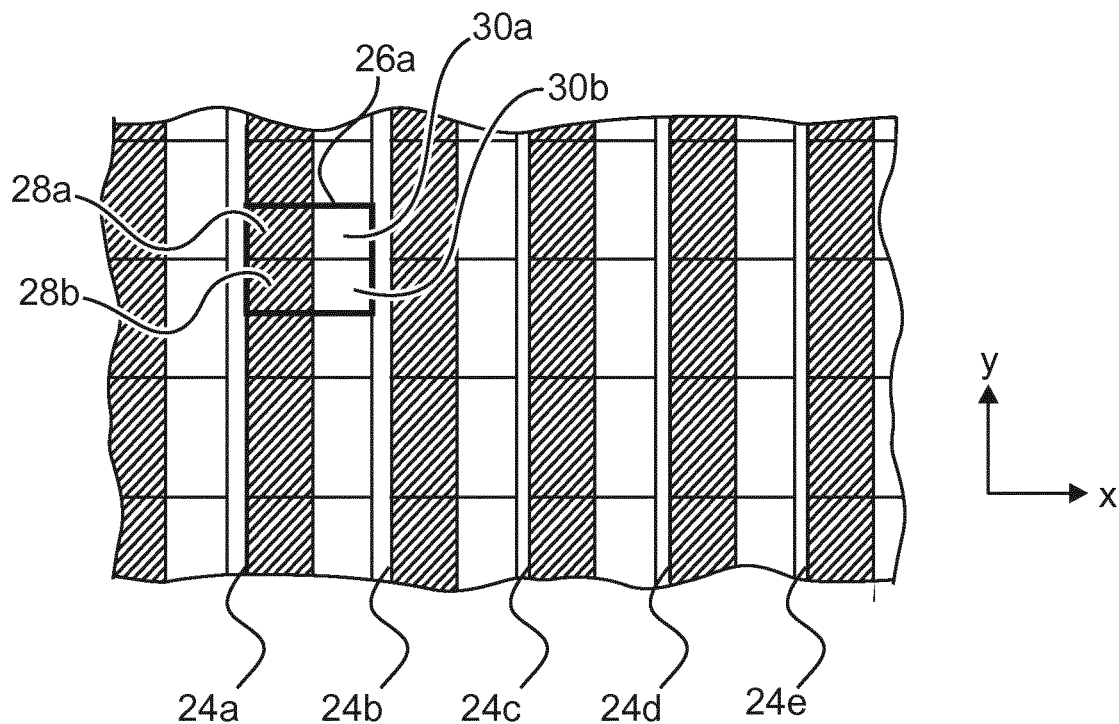
FIG. 3b) schematically illustrates an enlarged view of the front of an exemplary anti-scatter grid according to the first aspect.

FIG. 3b) schematically illustrates an enlarged front view corresponding to the inset of the adaptive anti-scatter device illustrated in FIG. 3a). Vertical slats 24a-e run in the y direction which, in operation, is transverse to a source to detector X-Ray beam axis, and the plane of the vertical slats defines the lateral surface of the adaptive anti-scatter filter that is directed towards an X-Ray source in operation.

The vertical slats 24a-e are realignably attached to a base member of the adaptive anti-scatter device, for example using a strip of resilient polymer that is attached to the slat and the base member. This enables the angle of the slat to change with respect to the source-detector axis 22.

Highlighted box 26a illustrates portion of an interstitial space. Interstitial space 26a comprises a first set of one or more actively deformable actuators (voxels) 28a, 28b. Although FIG. 3b) illustrates two actively deformable actuators 28a, 28b, it will be appreciated that the interstitial space 26a could comprise 1, 2, 3, 4, 5, 6, 7, 8, 9 or more actively deformable actuators. In other words, in a simple case the entire interstitial space 26a could comprise a single actuator. This is repeated for all, or a significant percentage, of the interstitial spaces of the adaptive anti-scatter device.

In the illustration, a portion of each of the actively deformable actuators 28a, 28b abut the vertical slats 24a so that when the actively deformable actuators 28a, 28b expand, at least slat 24a is realigned (moved in a direction substantially transverse to the source to detector axis) proportionately to the expansion of the actively deformable actuators 28a, 28b. Of course, the actively deformable actuators 28a, 28b may be designed only to produce expansion in a transverse direction away from the source-detector axis 22. Alternatively, the actively deformable actuators may be designed to contract in a transverse direction towards the source-detector axis 22. Furthermore, the behavior of the actively deformable actuator may be designed to vary based upon its coordinate on the lateral surface of the adaptive anti-scatter device 20.

In the illustrated case, interstitial space 26a also comprises non-essential inert elements 30a, 30b. These are not actively deformable.

Optionally, the inert elements 30a, 30b may comprise an inert and resilient element (such as elastic, rubber, or silicon) capable of changing shape as the actively deformable actuators expand and contract.

Optionally, the inert elements 30a, 30b may comprise an inert and hard substance (such as a plastic polycarbonate) that does not change shape as the actively deformable actuators expand and contract. The use of inert materials in portions of the interstitial space that is not occupied by an actively deformable actuator can enable the force generated by the actively deformable actuators 28a, 28b to be directed towards the slats in a controlled way.

For example, inert elements 30a, 30b are anchored to enable actively deformable actuators 28a, 28b to exert a transverse expansive or contractive force on realignable slat 24a, but to isolate realignable slat 24b from the transverse expansive or contractive force exerted by actively deformable actuators 28a, 28b.

It is not essential that the actively deformable actuators 28a, 28b directly about the slats 24 provided the force vector generated by their expansion or contraction can be transmitted to the slats 24. For example, the interstitial space 26a could comprise an outer donut-shaped ring of inert and resilient material, the inside of the donut-shaped ring comprising an actively deformable material. In this case, the inward or outward expansion force would be transmitted through the inert and resilient material to the slats.

In either the case of the actively deformable material 28a, 28b abutting the slats 24, and/or the inert material 30a, 30b abutting the slats 24 (where inert material is used), the actively deformable material 28a, 28b is provided so that it is partially, or fully recessed within the interstitial portions of the anti-scatter device 20. This enables the abutment (contact) of the actively deformable material 28a, 28b (or the inert material 30a, 30b) onto the surface of the slats, so that the expansion or contraction force can be transmitted. It is most preferable that the contact of the actively deformable material 28a, 28b (or the inert material 30a, 30b) onto the side of the slats occurs with a substantially zero air-gap, to enable accurate realignment of the slats as the actively deformable material 28a, 28b expands and contracts.

Figure 3C:
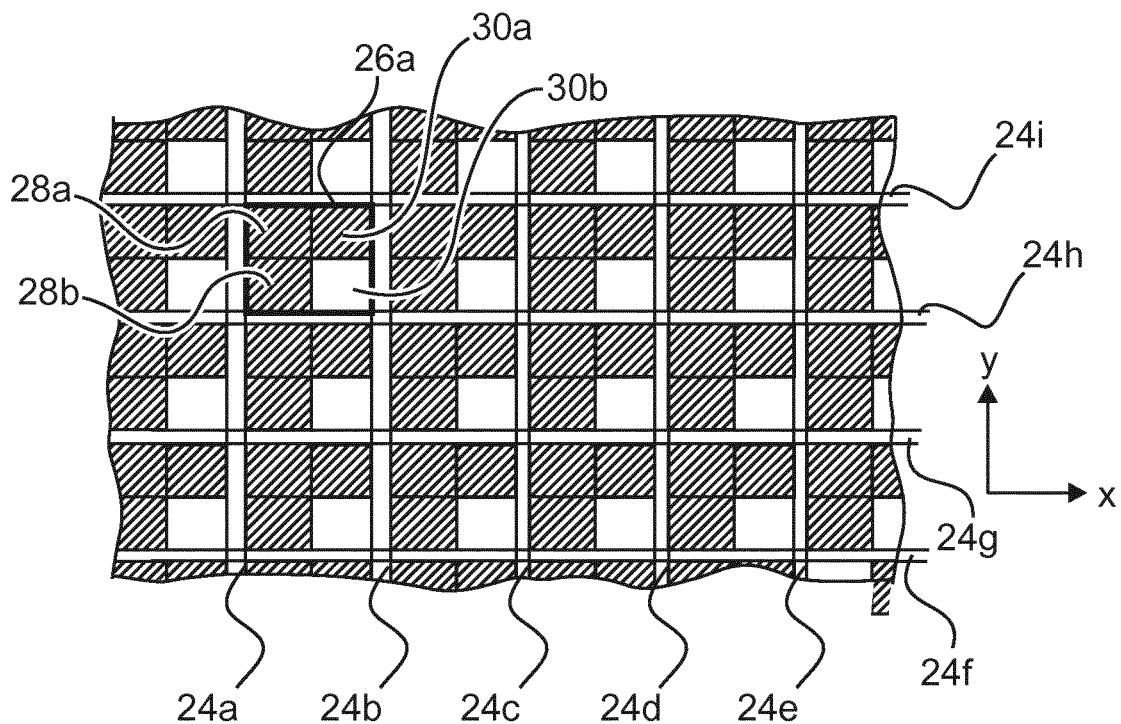
FIG. 3c) schematically illustrates a front view of an exemplary 2D embodiment of the anti-scatter grid according to the first aspect.

FIG. 3c) schematically illustrates a front view of an exemplary 2D embodiment of the anti-scatter grid according to the first aspect.

Figure 4A:
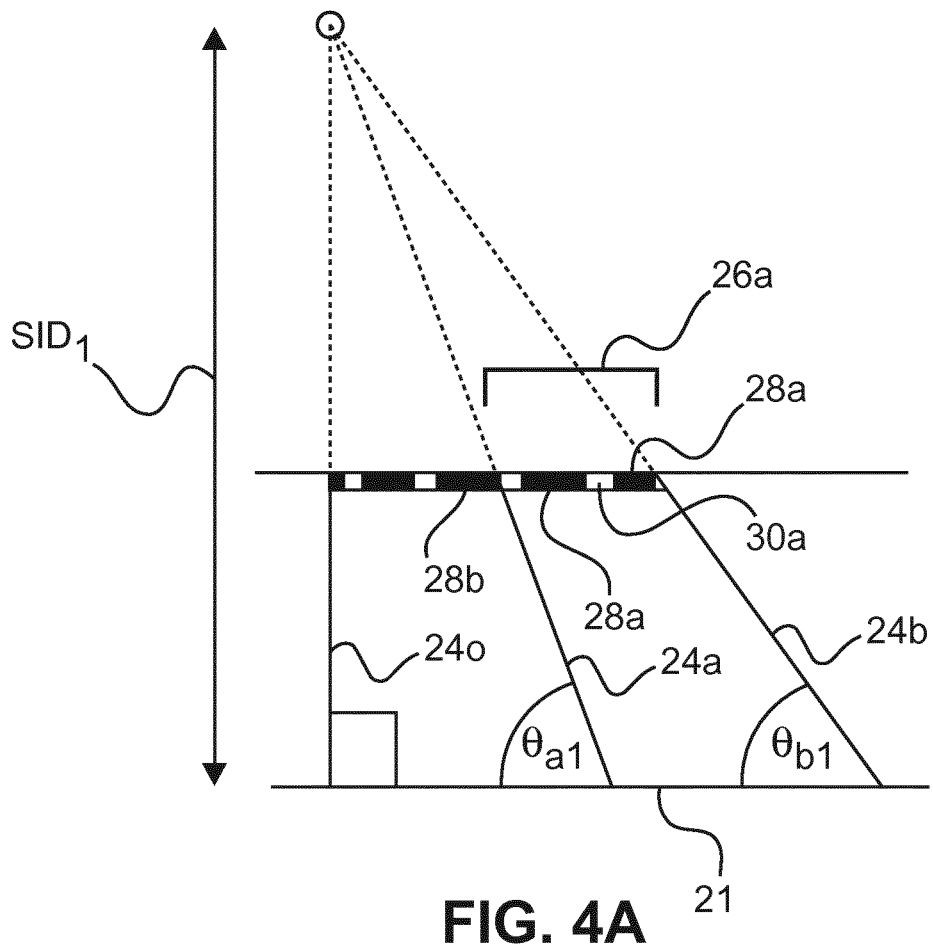
FIG. 4a) schematically illustrates a side view of an exemplary anti-scatter grid according to the first aspect in a first configuration.

The anti-scatter grid illustrated in FIGS. 3a) and 3b) comprises a first plurality of parallel slats (lamellae) aligned in a first direction allowing the redirection of the grid along one axis. The embodiment of FIG. 3c) extends this concept by providing, in addition, a second plurality of slats 24f, 24g, 24h, 24i aligned transverse to the first plurality of slats. The slats of the second plurality of slats 24f, 24g, 24h, 24i are provided with cut-outs (not shown) at junctions between the slats of the first and second pluralities of slats. The function of the cutouts is to allow the slats of the first plurality of slats to adjust their angle without colliding with the slats of the second plurality of slats. Furthermore, an additional set of 3D or 4D printed actuators abutting the slats of the second plurality of slats are provided to function to manipulate the angle of the slats of the second plurality of slats in the same manner as actuators 28a and 28b in relation to the first plurality of slats. Accordingly, an adjustable 2D anti-scatter grid may also be provided. FIG. 4a) schematically illustrates a side view of an exemplary anti-scatter grid according to the first aspect in a first (relaxed) configuration. In this figure, a side view of slats 24a, 24b, is given. Slat $24_0$ is perpendicular to the base member 21. Slat 24a initially encloses an angle of $\vartheta_{a1}$. Slat 24b initially encloses an angle of $\vartheta_{b1}$. The first actively deformable member 26a comprises actively deformable actuator 28a abutting 24a. Furthermore, the first actively deformable member 26a comprises a non-essential inert, or less deformable member 30a. This configuration is appropriate for the source to image distance $SID_1$ (a first alignment) enabling good separation of scattered X-radiation.

Figure 4B:
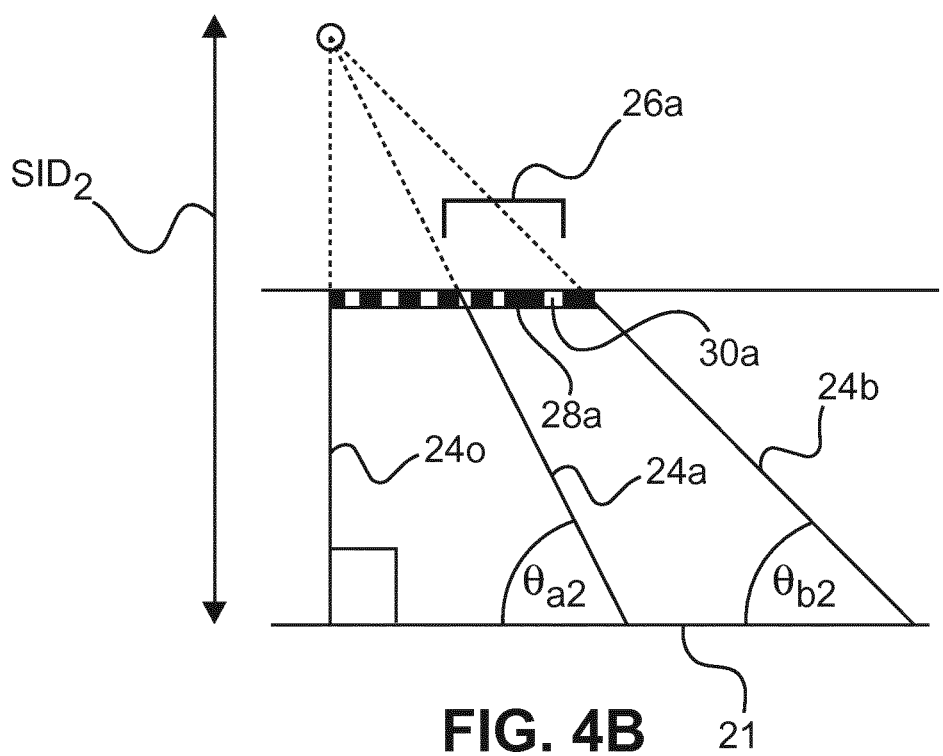
FIG. 4b) schematically illustrates a side view of an exemplary anti-scatter grid according to the first aspect in a second configuration.

FIG. 4b) schematically illustrates a side view of an exemplary anti-scatter grid according to the first aspect in a second (contracted) configuration. The source to image distance $SID_2$ has been moved closer to the adaptive anti-scatter grid, necessitating a change in angulation of the slats 24a, and 24b. Accordingly, a control signal (not shown) causes the first actively deformable member 26a to contract, thus reducing the enclosed angles of the slats $\vartheta_{b1}$ and $\vartheta_{b2}$ to angles (a second alignment) appropriate for good X-Ray scatter rejection at the source position $SID_2$.

Although not illustrated, a cover element that is translucent X-rays may be provided to cover at least one side of the adaptive anti-scatter device to provide mechanical protection, for example. Slats of the anti-scatter grid may, in this case, be coupled to the cover element using a resilient material that enables re-angulation of the slats.

Optionally, the anti-scatter device further comprises a second actively deformable member comprising a third set of one or more actively deformable actuators configured to change the alignment of a corresponding slat of the anti-scatter filter in relation to the source-detector axis. One or more actively deformable actuators of the third set of one or more actively deformable actuators is formed within the interstitial portions of the anti-scatter filter and in contact with at least one corresponding slat of the plurality of slats, so that a deformation of an actively deformable actuator of the third set of one or more actively deformable actuators causes a corresponding change to the alignment of the at least one corresponding slat relative to the source-detector axis.

The second actively deformable member is provided in lateral alignment with the first actively deformable member along the source detector axis. In other words, an adaptive anti-scatter device according to this embodiment comprises a layered structure of first and second actively deformable members. Of course, third, fourth, fifth, and more layers of actively deformable members may be provided. The additional layers of actively deformable members optionally actuated using a unified control signal, to ensure that they expand in proportion to each other (to avoid bending or curling the slats). By providing additional layers of actively deformable members abutting the slats at the depth of the respective additional layers of actively deformable members, a more rigid attachment of the slats is provided.

Accordingly, a second actively deformable member positioned in the anti-scatter device further from a source position than the first actively deformable member may comprise a smaller lateral spatial density of actively deformable actuators compared to the first actively deformable member.

Accordingly, a third actively deformable member positioned in the anti-scatter device further from a source position than the second actively deformable member may comprise a smaller lateral spatial density of actively deformable actuators compared to the second actively deformable member.

Optionally, a member positioned in the anti-scatter device further strong source position compared to other actively deformable members may be comprised entirely of inert material to function as a slat former.

By varying the lateral spatial density of actively deformable actuators abutting the anti-scatter grid in each layer of actively deformable members in the adaptive anti-scatter device, account is taken that the slats will each need to be moved at their greatest lateral displacement AA, AB at the lateral face of the adaptive anti-scatter device closest to the source. For a layer of actively deformable members at the layer of the anti-scatter device furthest from the source direction, a small or zero lateral displacement of the slat is required. For an actively deformable member placed substantially in the middle of the depth of the anti-scatter device, a middling displacement of the slats in between the extremes of slat displacement required at the outer faces of the anti-scatter device is required. Accordingly, the lateral spatial density of actively deformable actuators is optionally greater on a first actively deformable member of an adaptive anti-scatter device that is closest to an X-Ray source, and the lateral spatial density of actively deformable actuators is optionally smaller on a third or second actively deformable member that are further away from the X-Ray source.

Figure 5A:
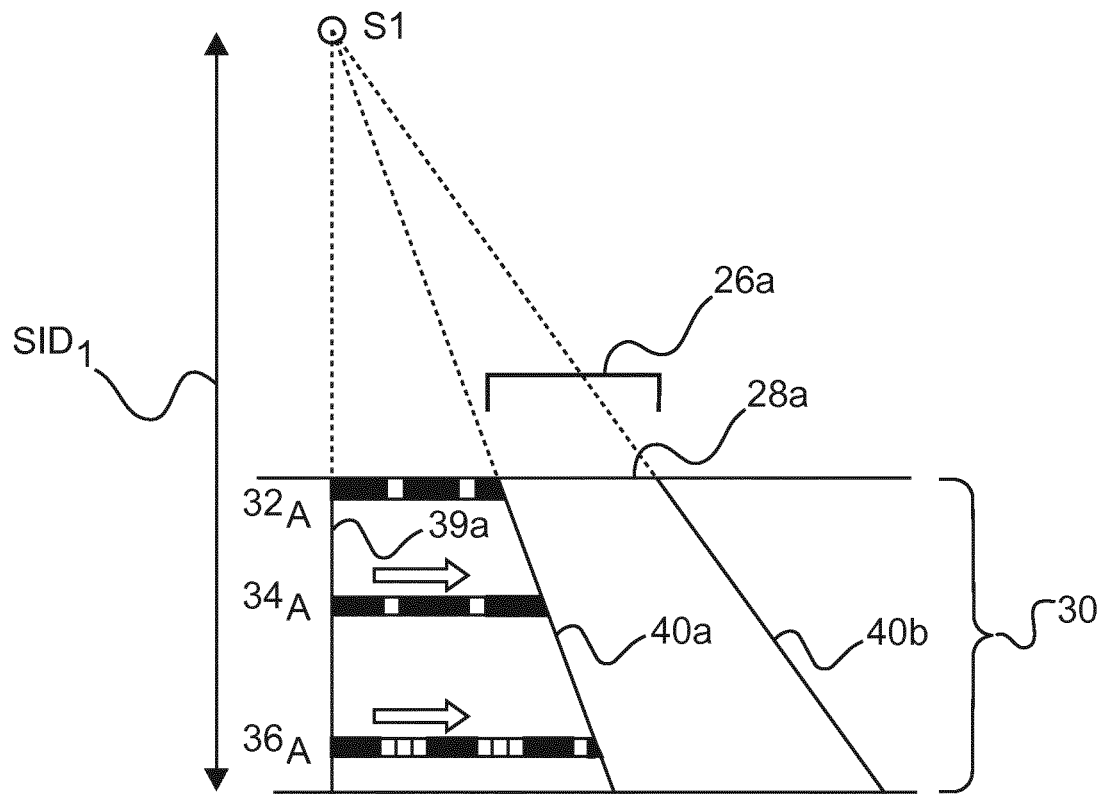
FIG. 5 schematically illustrates a side view of a further exemplary anti-scatter grid according to the first aspect superimposed into two separate configurations.
Figure 5B:
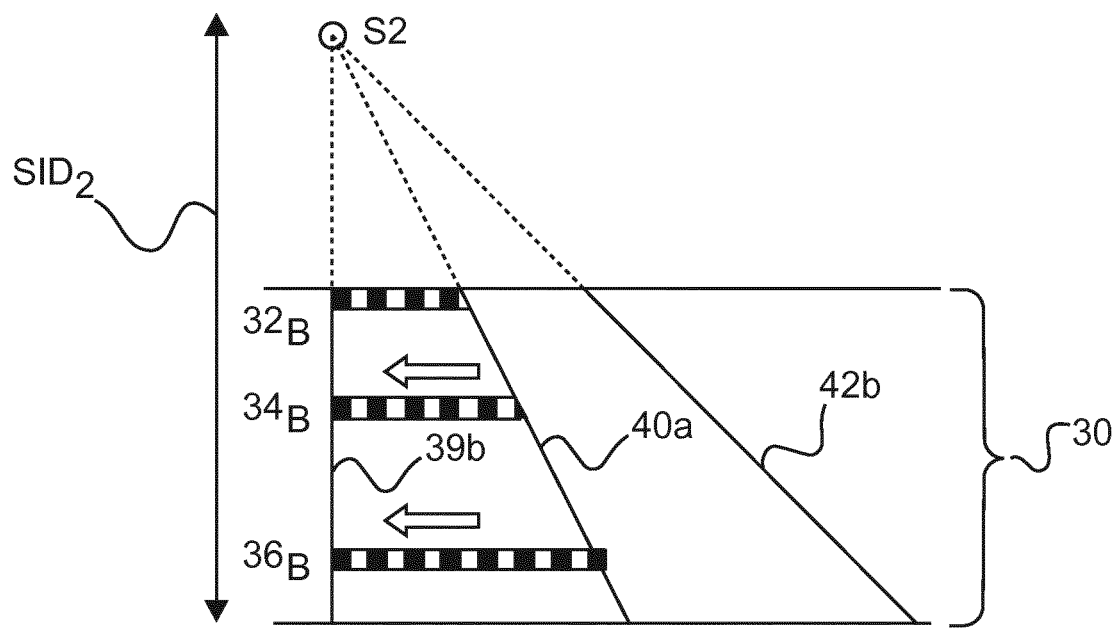

FIGS. 5a) and b) schematically illustrate side views of an adaptive anti-scatter device 30 in a first and a second state. The illustrated adaptive anti-scatter device 30 is similar to that illustrated in FIGS. 4a) and b), and comprises three layers of actively deformable members: an upper layer 32 closest to a variable X-Ray source position $S_1$, $S_2$, a middle layer 34, and a bottom layer 36 furthest from a variable X-Ray source position $S_1$, $S_2$. The three layers of actively deformable members about the slat 39 and 40. A similar set of three layers of actively deformable members would be provided between slats 40 and 42. FIG. 5a) illustrates the configuration of the actively deformable members in an uncontracted position $32_A$, $34_A$, $36_A$. FIG. 5b) illustrates the configuration of the actively deformable members in a contracted position $32_B$, $34_B$, $36_B$. As shown, the first actively deformable member 32 closer to the X-Ray source must expand and contract with a greater displacement as compared to the third actively deformable member 36.

Notably, the actively deformable actuator applied in the first, second, and/or third actively deformable members may act to contract or to expand, dependent on the material or design of the actively deformable actuator.

Although FIG. 5 illustrates an adaptive anti-scatter device comprising three actively deformable members at different times, it is not excluded that an adaptive anti-scatter device comprising two actively deformable members at different layers of the adaptive anti-scatter device is provided.

The ratio between active and less active actuators determines what the maximum contraction (or expansion) force and distance is between two slats (lamellae) at a certain location of the filter. The difference in contraction between the top side and the bottom side (source facing and detector facing sides) determines the orientation of the slats. Additionally, progressively more off-axis slats may need to be angled at a greater rate than the slats closer to the source to detector. Thus, a greater number of active elements, or an active element capable of a greater displacement change, may be required closer towards the extremities of the filter as compared with the source to detector axis. Of course, smaller 3D printed actuators enable more precise steering of the slats. Typically, an anti-scatter filter (grid) may have 44 lines per centimeter, and an actuator size of around 25 to 30 microns, allowing approximately 10 actuators to fit in the interstitial space of a typical grid. The number of actuators that may be fitted into the interstitial space of a typical grid is variable based on the type of grid, and the type of 3D or 4D printing used to construct the actuators.

Optionally, the first actively deformable member further comprises a second set of one or more actively deformable actuators disposed in a second region of the first actively deformable member. The first region is laterally closer to the source-detector axis than the second region. The second region of the first actively deformable member comprises a greater spatial density of actively deformable actuators than the first region.

Figure 6:
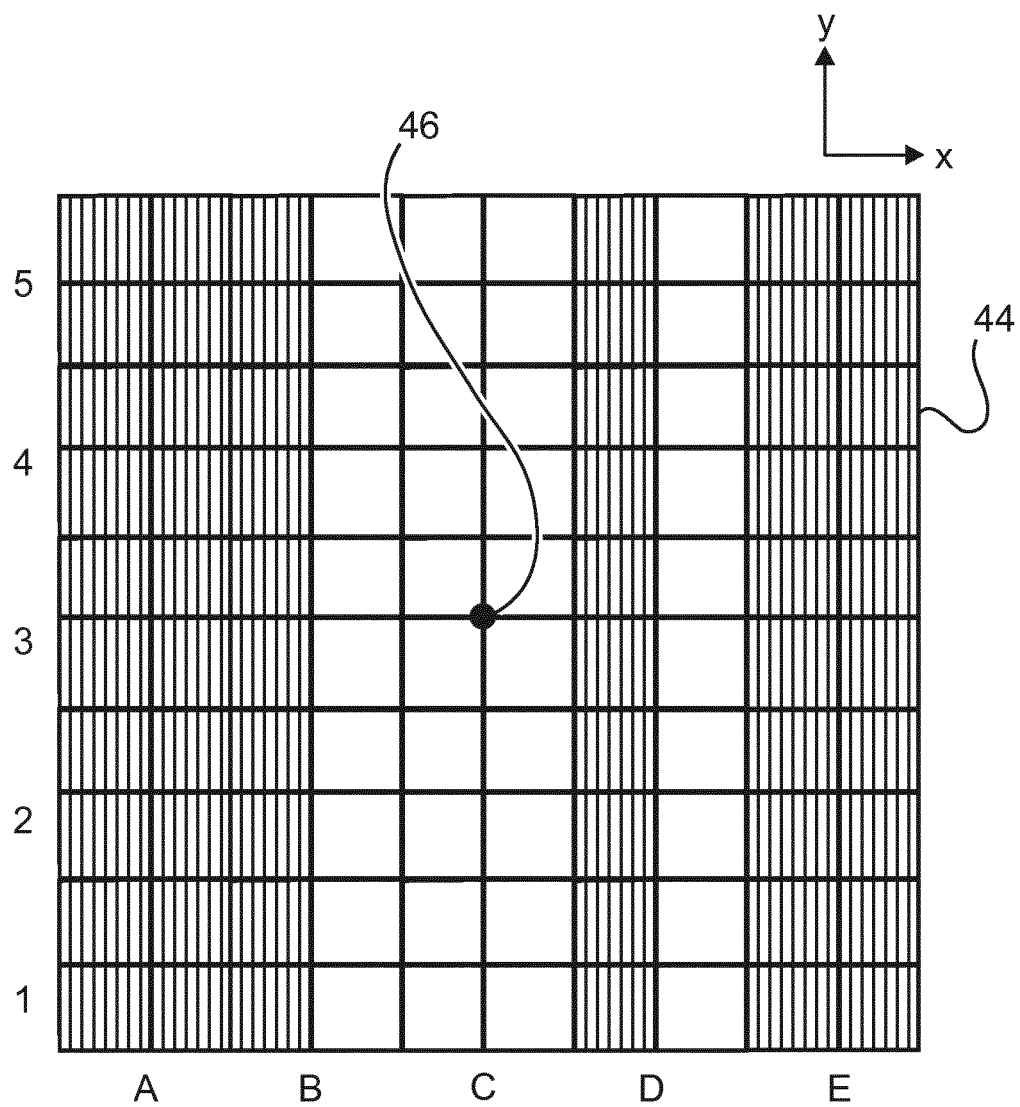
FIG. 6 schematically illustrates a front view of a further exemplary anti-scatter grid comprising a varying lateral spatial density of active actuators.

FIG. 6 schematically illustrates a front view of a further exemplary anti-scatter filter 44 comprising a varying lateral spatial density of active actuators. The number of actively deformable actuators has been reduced in this representation to enable clearer understanding. The anti-scatter filter 44 comprises a first plurality of actively deformable actuators that will be referenced along a first lateral direction using the coordinates A-E and along a second lateral direction using the coordinates 1-5. Thus, the source-detector center axis 46 is located in C3. The actively deformable actuators are shown grouped into square groups of four with inert (or less deformable) portions.

Optionally, member C3 containing the source-detector axis 46 does not comprise an actively deformable actuator because it is located on the source-detector center axis 46. It may be comprised of an air gap, or an inert resilient or non-resilient material, for example. Alternatively however, member C3 may comprise an actively deformable actuator. The line C1, C2, C3, C4, C5 likewise does not comprise deformable actuators.

In FIG. 6, the members either side of the source-detector axis 46 in columns B and D comprise a first region of actively deformable actuators (filled squares) forming substantially one half of the space inside the interstitial region between slats separating the actively deformable actuators. The remainder of the space inside the interstitial regions of these actuators may optionally be empty (comprised of air), or comprised of a resilient or non-resilient inert material (such as plastic or silicone, for example).

Moving laterally further away from source-detector axis 46, the lines of members in columns A and E comprise a second region of actively deformable actuators (filled squares) occupying substantially all of space inside each interstitial region between slats separating the actively deformable actuators in other words, the second region of actively deformable actuators further from the source-detector axis has a greater lateral spatial density of actively deformable actuators compared to the first region of actively deformable actuators that are close to the source-detector axis 46. Accordingly, in this embodiment the density of the actively deformable actuators increases as the lateral distance across the grid from the source to detector axis increases.

In operation (and assuming that the actively deformable actuators illustrated all provide an equal displacement), actively deformable actuators of columns A and E tend to deflect the slats of the adaptive anti-scatter filter 44 in the X and Y directions to a greater extent compared to actively deformable actuators of the first region. Accordingly, scattered X-Ray radiation can be effectively filtered at different lateral regions of an X-Ray detector. It is not essential that the first and second regions of actively deformable actuators contain different integer numbers of actively deformable actuators. For example, each interstitial space in actively deformable members A-E, 1-5 may comprise one actively deformable actuator configured to expand or contract by the same amount upon the application of the driving signal. Optionally, each interstitial space in actively deformable members A-E, 1-5 may comprise one actively deformable actuator configured to expand or contract by a different amount upon the application of the driving signal depending on its location either in the first or the second region. This may be achieved by, for example, depositing a larger or smaller deposit of electro-active polymer at the relevant actuator location, for example.

Optionally, the actuators of the first and/or second actively deformable member are controllable with a unified control signal, or the actuators of the first and/or second actively deformable member are divided into individually addressable actuator regions.

FIG. 6 illustrates a 1D anti-scatter grid with grids in the y direction only, having a variation in density of the deformable actuators with lateral distance from the source to detector axis in the x direction.

However, an adaptive X-ray anti scatter grid may be provided having slats in the X and Y direction. In this case, a 2D variation in density of the deformable actuators with lateral distance from the source to detector axis can be provided.

Figure 7:
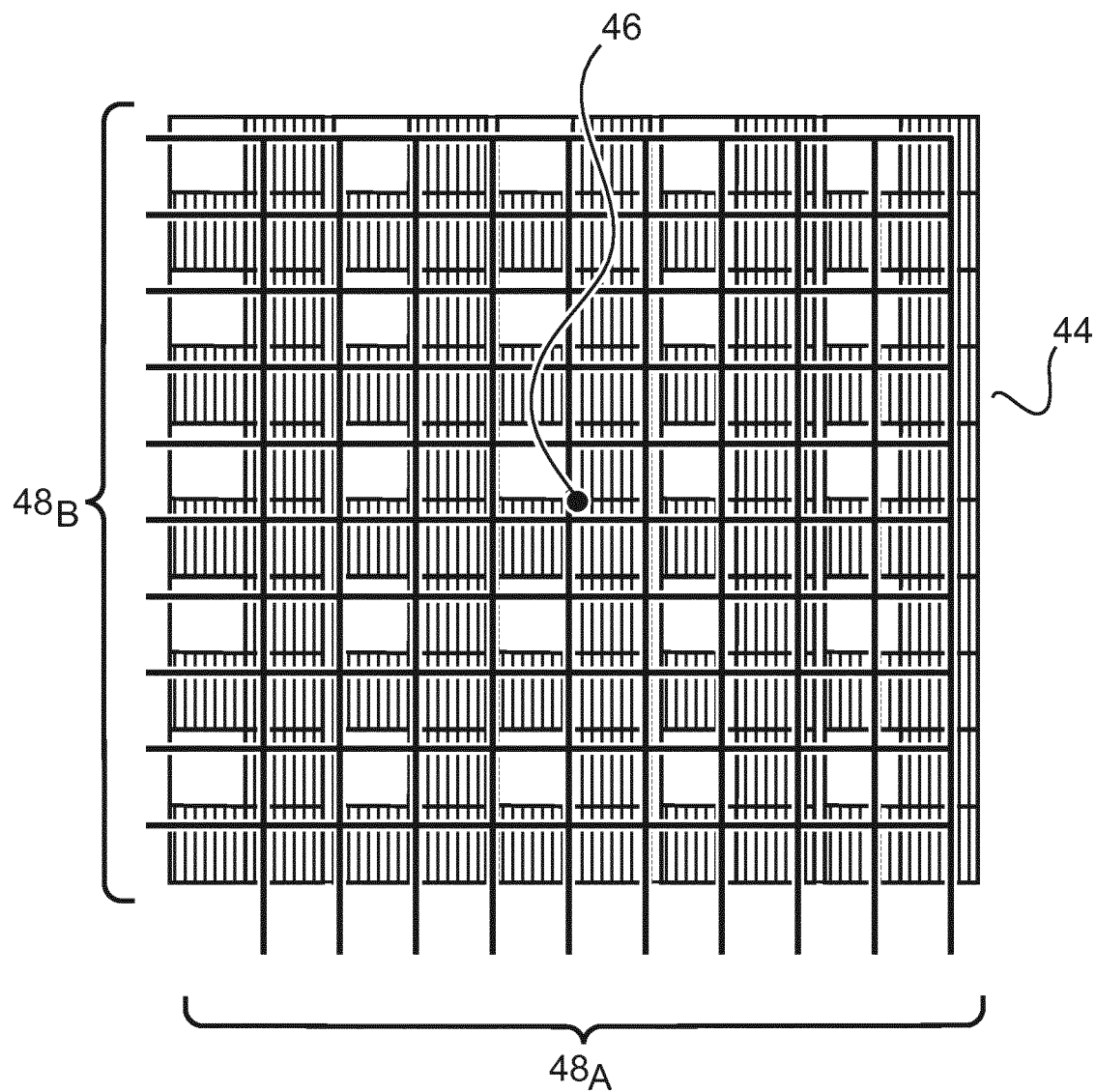
FIG. 7 schematically illustrates a front view of a further exemplary anti-scatter grid comprising a control signal arrangement.

Furthermore, in a 1D anti-scatter grid with grids in the y direction only, a 2D variation in density of the deformable actuators with lateral distance from the source to detector axis can be provided in order to provide a non-equal deflection of the slats in x direction of a 1D grid. FIG. 7 schematically illustrates a front view of a further exemplary anti-scatter filter of FIG. 6 additionally comprising a control signal arrangement $48_A$, $48_B$. The control signal arrangement $48_A$, $48_B$ enables a signal controlling the deformation of actively deformable actuators to be conveyed from a control means to a plurality of actively deformable actuators. As will be appreciated, the control signal arrangement $48_A$, $48_B$ depends on the type of actively deformable actuator used. In the case of electro-active polymers or thermally active alloys, the control signal may, for example, be a digital electronic signal or an analogue electronic signal brought into electrical contact with the electro-active polymer or a heater near the thermally active alloy. In the case that the actively deformable actuator is a microfluidic inflatable or deflatable element, the control signal may, for example, be a microfluidic channel capable of carrying a gas or a non-compressible liquid. Furthermore, the control signal arrangement $48_A$, $48_B$ can enable the unified addressing of all actively deformable actuators of the entire adaptive anti-scatter device (requiring a less complicated control circuit). Alternatively, the control signal arrangement $48_A$, $48_B$ can enable the specific addressing of individual actively deformable actuators, sub-groups of actively deformable actuators, or specific layers of actively deformable actuators.

Figure 8:
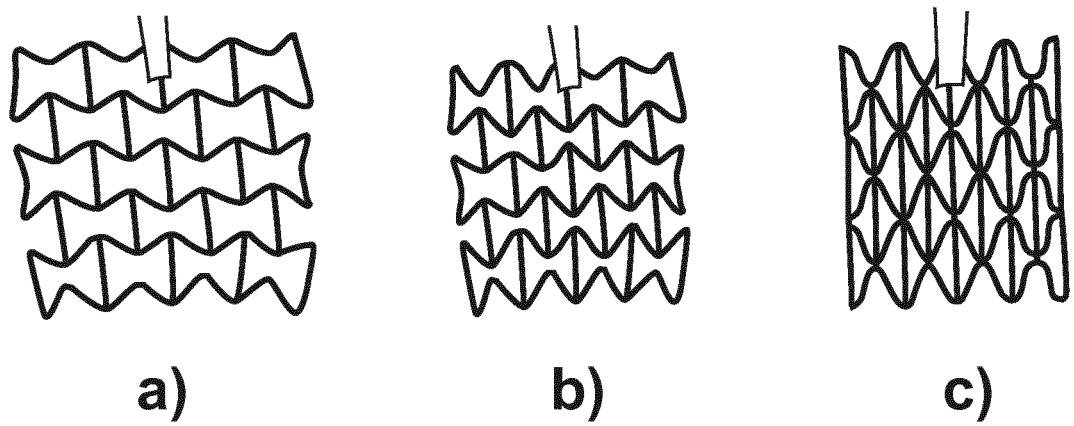
FIGS. 8a) to c) schematically illustrate a deformable auxetic contraction cell in various degrees of contraction.
Figure 9:
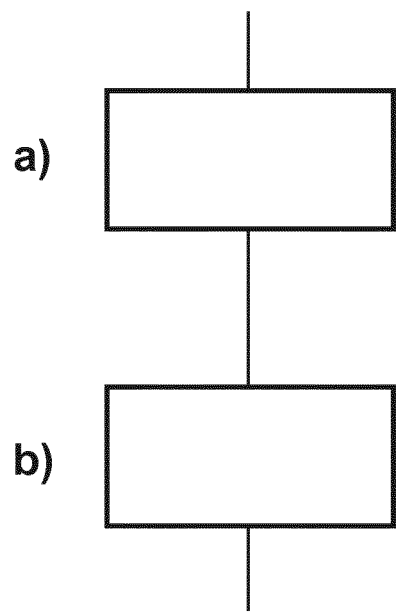
FIG. 9 schematically illustrates a method according to the fourth aspect.

FIGS. 8a) to c) schematically illustrate a deformable auxetic contraction cell in various degrees of contraction. Accordingly, an actively deformable actuator can be provided as an auxetic contraction (or expansion) cell. Alternatively or in combination, an actively deformable actuator is provided as a combination of a deformable auxetic contraction cell with a portion of electro-active polymer or the other techniques discussed previously.

According to a second aspect, there is provided an X-ray detector assembly comprising:
an X-ray detector, and
at least one adaptive anti-scatter device according to the first aspect or its embodiments.

For example, the X-Ray detector assembly comprises a flat-panel digital X-Ray detector is known to a person skilled in the art, with the at least one adaptive anti-scatter device mounted onto the source-facing side of the flat-panel digital X-Ray detector.

According to a third aspect, there is provided an X-ray imaging system 8 having a variable source-imaging distance $SID_1$, $SID_2$ comprising:
an X-ray source 12 configured to emit a beam of X-ray radiation directed towards a patient imaging area 14 of the X-ray imaging system along a source-detector axis;
an X-ray detector assembly 16 according to the second aspect configured to detect X-ray radiation emitted from the X-ray source; and
a controller 19 configured to provide a control signal to the first actively deformable member of the adaptive anti-scatter device of the X-ray detector.

The X-ray source 12 and/or the X-ray detector 16 are configurable so that they can be separated by at least a first $SID_1$ and a second $SID_2$ different source detector distance.

The controller 19 is configured to monitor the source detector distance of the X-ray source and X-ray detector, and to generate a control signal for the first actively deformable member, to set the first actively deformable member using the control signal, and to obtain X-ray imaging data from the X-ray detector 16 with the first actively deformable member configured at an appropriate alignment for the source detector distance of the X-ray source and X-ray detector.

Optionally, the controller 19 is configured to obtain source detector separation information from the X-Ray imaging system control software, and/or from sensors inside the X-Ray imaging system motion drive circuitry.

The controller 19 is configured to output control signals to the adaptive anti-scatter device configured to adjust actively deformable actuators so that slats in the anti-scatter device are removed from a first alignment to a second alignment relative to the source-detector axis, to enable an appropriate slat alignment to provide for a given source detector separation distance. For example, the output control signals may be generated by a lookup table, a mathematical function, or by an online feedback loop that monitors the quality of the received image and makes minor adjustments to the alignment of the slats to reduce scatter.

According to a fourth aspect, there is provided a method for manufacturing an adaptive anti-scatter device comprising:
 a) providing an anti-scatter filter having a source orientable surface and a detector orientable surface, wherein the anti-scatter filter comprises a plurality of realignable slats for absorbing incident X-rays, wherein the realignable slats are separated by a plurality of interstitial portions; and
 b) providing a first actively deformable member comprising a first set of one or more actively deformable actuators disposed across a first region of the first actively deformable member, wherein one or more of the first set of one or more actively deformable actuators are configured to change the alignment of a corresponding slat of the anti-scatter filter in relation to the source-detector axis. At least a portion of one or more of the first set of one or more actively deformable actuators is partially or fully recessed within the interstitial portions of the anti-scatter filter. One or more of the first set of actively deformable actuators is in contact with at least one realignable slat of the plurality of slats, so that a deformation of the at least one of the first set of one or more actively deformable actuators causes a corresponding change to the alignment of the at least one corresponding slat from a first alignment to a second alignment relative to the source-detector axis.

The method of manufacturing an adaptive anti-scatter-device using 3D printing may comprise providing the first actively deformable member as a sub-component to be integrated with a previously manufactured anti-scatter grid.

For example, the X-Ray absorbing slats could be provided as metal sheets (such as molybdenum or tungsten) fixed on a first side in a plastic carrier having fixed pitch, and on the source-facing side with first actively deformable members as discussed previously. Alternatively, a 3D printer may be used simultaneously to print the grid and the actively deformable members.

According to a fifth aspect, there is provided a computer program element comprising instructions for the operation of a 3D or 4D printer which, when addressed to a 3D or 4D printer, cause the 3D or 4D printer to follow the method of the fourth aspect. For example, the computer program element may comprise instructions in common 3D or 4D printer file formats such as STL, OBJ, FBX, COLLADA, 3DS, IGES, STEP, and VRML/X3D. These files may be compiled using 3D or 4D printer design software is known in the art.

According to a sixth aspect, there is provided a computer readable medium comprising instructions for the operation of a 3D or 4D printer of the fifth aspect.

A computer program element might therefore be stored on a computer unit, which might also be an embodiment of the present invention. This computing unit may be adapted to perform or induce performance of the steps of the method described above. The computing unit can be adapted to operate automatically and/or to execute orders of a user. A computer program may be loaded into a working memory of a data processor. The data processor may thus be equipped to carry out the method of the invention.

This exemplary embodiment of the invention covers both a computer program that has the invention installed from the beginning, and a computer program that by means of an update turns an existing program into a program that uses the invention.

The 3D or 4D printer data can be provided to a 3D or 4D printer over a local area network, or save on physical media such as a digital versatile disc, tape drive, or USB stick. The 3D or 4D printer data may be stored and/or distributed on a suitable medium, such as optical storage media, or a solid-state medium supplied together with, or as part of other hardware, but may also be distributed in other forms such as via the Internet or other wired or wireless telecommunication systems. However, the computer program may also be presented over a network like the World Wide Web, and can also be downloaded into the working memory of a data processor from such a network.

It should be noted that aspects and embodiments of the invention have been described with reference to different subject matter. In particular, some embodiments are described with reference to method-type claims, whereas other embodiments are described with reference to device-type claims. A person skilled in the art will, however, gather from the above and following description, that, unless otherwise notified, in addition to any combination of features belonging to one type of subject-matter, also any combination between features related to different subject-matter is considered to be disclosed with this application. All features discussed herein can be combined providing synergetic effects that are more than simply a summation of the features. While the invention has been illustrated and described in detail in the drawings and foregoing description, such illustration and description are to be considered illustrative or exemplary, and not restrictive. The invention is not limited to the disclosed embodiments. Other variations to the disclosed embodiments can be understood and effected by those skilled in the art practicing the claimed invention from a study of the drawings. The disclosure, and the dependent claims.

In the claims, the word "comprising" does not exclude other elements or steps and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An adaptive X-ray anti-scatter device for placement in a source-detector axis of an X-ray imager comprising:
 an anti-scatter filter having a source orientable surface and a detector orientable surface, wherein the anti-scatter filter comprises a plurality of realignable slats for absorbing incident X-rays, wherein the plurality of realignable slats are separated by a plurality of interstitial portions; and
 a first actively deformable member comprising a first set of one or more actively deformable actuators disposed across a first region of the first actively deformable member,
 wherein at least a portion of the first set of one or more actively deformable actuators is partially or fully recessed within the plurality of interstitial portions of the anti-scatter filter, and
 wherein at least one actuator of the first set of one or more actively deformable actuators is in contact with a corresponding at least one realignable slat of the plurality of realignable slats, the at least one actuator being configured to change alignment of the corresponding at least one realignable slat in relation to the source-detector axis.

2. The adaptive anti-scatter device according to claim 1, further comprising:
a cover element arranged to cover at least one side of the adaptive anti-scatter device, wherein the plurality of realignable slats of the anti-scatter filter are coupled to the cover element.

3. The adaptive anti-scatter device according to claim 1, wherein a lateral spatial density of actively deformable actuators of the first actively deformable member varies as a function of a lateral location on the first actively deformable member.

4. The adaptive anti-scatter device according to claim 1, wherein the first actively deformable member further comprises:
a second set of one or more actively deformable actuators disposed in a second region of the first actively deformable member;
wherein the first region is laterally closer to the source-detector axis than the second region;
wherein the second region of the first actively deformable member comprises a greater spatial density of actively deformable actuators than the first region.

5. The adaptive anti-scatter device according to claim 4, wherein at least one of the first set of one or more actively deformable actuators, the second set of one or more actively deformable actuators, and a third set of one or more actively deformable actuators comprise actively deformable actuators of an electro-active or thermally-active polymer or metal alloy.

6. The adaptive anti-scatter device according to claim 1, further comprising:
a second actively deformable member comprising a third set of one or more of actively deformable actuators configured to change the alignment of a corresponding realignable slat of the anti-scatter filter in relation to the source-detector axis,
wherein one or more actuators of the third set is formed within the plurality of interstitial portions of the anti-scatter filter and in contact with at least one corresponding realignable slat of the plurality of realignable slats, so that a deformation of an actively deformable actuator of the third set of one or more actively deformable actuators causes a corresponding change to the alignment of the at least one corresponding realignable slat relative to the source-detector axis.

7. The adaptive anti-scatter device according claim 6, wherein the second actively deformable member is located closer to a source-orientable face than the first actively deformable member; and wherein a lateral spatial density of actively deformable actuators of the second actively deformable member is greater than a lateral spatial density of actively deformable actuators of the first actively deformable member at corresponding lateral positions of the first actively deformable member and the second actively deformable member.

8. The adaptive anti-scatter device according claim 6, wherein the plurality of interstitial spaces of the anti-scatter filter comprise actuators of at least one of the first actively deformable member and the second actively deformable member, wherein one or more of the plurality of interstitial spaces comprise a first set of one or more actively deformable actuators, and a second plurality of non-deformable actuators, or actuators that are less deformable than the actuators in the first set of one or more actively deformable actuators.

9. The adaptive anti-scatter device according to claim 6, wherein the actuators of at least one of the first actively deformable member and the second actively deformable member are controllable with a unified control signal, or the actuators of at least one of the first actively deformable member and the second actively deformable member are divided into individually addressable actuator regions.

10. An X-ray detector comprising:
at least one adaptive anti-scatter device according to claim 1.

11. An X-ray imaging system having a variable source-imaging distance comprising:
an X-ray source configured to emit a beam of X-ray radiation directed towards a patient imaging area of the X-ray imaging system along a source-detector axis;
an X-ray detector according to claim 10 configured to detect X-ray radiation emitted from the X-ray source; and
a controller configured to provide a control signal to the first actively deformable member of the adaptive anti-scatter device of the X-ray detector;
wherein the X-ray source and/or the X-ray detector are configurable to be separable by a source detector distance; and
wherein the controller is configured to monitor the source detector distance of the X-ray source and the X-ray detector, to generate a control signal for the first actively deformable member, to set the first actively deformable member using the control signal, and to obtain X-ray imaging data from the X-ray detector with the first actively deformable member configured for the source detector distance of the X-ray source and the X-ray detector.

12. A method for manufacturing an adaptive anti-scatter device comprising:
a) providing an anti-scatter filter having a source orientable surface and a detector orientable surface, wherein the anti-scatter filter comprises a plurality of realignable slats for absorbing incident X-rays, wherein the plurality of realignable slats are separated by a plurality of interstitial portions;
b) providing a first actively deformable member comprising a first set of one or more actively deformable actuators disposed across a first region of the first actively deformable member, including:
c) providing at least a portion of the first set of one or more actively deformable actuators within the plurality of interstitial portions of the anti-scatter filter in a partially or fully recessed manner, and
d) contacting at least one actuator of the first set of one or more actively deformable actuators with a corresponding at least one realignable slat of the plurality of realignable slats such that a deformation of the at least one actuator causes a change of alignment of the corresponding at least one realignable slat in relation to a source-detector axis.

13. The method for manufacturing an adaptive anti-scatter device according to claim 12, wherein at least one of a) and b) are performed using a 3D or a 4D printer.

14. A non-transitory computer-readable storage medium having stored a computer program comprising instructions for operation of a 3D printer or 4D printer for manufacturing an adaptive anti-scatter device, the instructions, when executed by a processor, cause the 3D printer or the 4D printer to:
- provide an anti-scatter filter having a source orientable surface and a detector orientable surface, wherein the anti-scatter filter comprises a plurality of realignable slats for absorbing incident X-rays, wherein the plurality of realignable slats are separated by a plurality of interstitial portions;
- provide a first actively deformable member comprising a first set of one or more actively deformable actuators disposed across a first region of the first actively deformable member, including:
- provide at least a portion of the first set of one or more actively deformable actuators within the plurality of interstitial portions of the anti-scatter filter in a partially or fully recessed manner, and
- contact at least one actuator of the first set of one or more actively deformable actuators with a corresponding at least one realignable slat of the plurality of realignable slats such that a deformation of the at least one actuator causes a change of alignment of the corresponding at least one realignable slat in relation to a source-detector axis.

* * * * *